United States Patent [19]

Marinovic

[11] Patent Number: 4,743,632
[45] Date of Patent: May 10, 1988

[54] POLYETHERURETHANE UREA POLYMERS AS SPACE FILLING TISSUE ADHESIVES

[75] Inventor: N. Nash Marinovic, Groton, Conn.

[73] Assignee: Pfizer Hospital Products Group, Inc., New York, N.Y.

[21] Appl. No.: 18,546

[22] Filed: Feb. 25, 1987

[51] Int. Cl.$^4$ ............................................ C08G 18/32
[52] U.S. Cl. ........................................ 523/118; 524/839; 528/59; 528/60; 528/61; 528/62; 523/16; 523/66
[58] Field of Search ................. 523/118; 524/839; 528/59, 60, 61, 62; 623/16 C, 66

[56] References Cited

U.S. PATENT DOCUMENTS

| | | | |
|---|---|---|---|
| 2,929,804 | 3/1960 | Steuber | 260/77.5 |
| 3,271,352 | 9/1966 | Weinberg | 260/37 |
| 3,384,624 | 5/1968 | Heiss | 260/77.5 |
| 3,415,790 | 10/1968 | Davis et al. | 260/77.5 |
| 3,752,786 | 8/1973 | Rossitto et al. | 260/33.4 |
| 3,883,577 | 5/1975 | Rabizzoni et al. | 260/471 |
| 4,062,834 | 12/1977 | Gilding et al. | 260/77.5 |
| 4,169,175 | 9/1979 | Marams et al. | 528/59 |
| 4,385,171 | 5/1983 | Schobel et al. | 528/491 |
| 4,477,604 | 10/1984 | Oscheda et al. | 523/116 |
| 4,560,555 | 12/1985 | Snider | 424/78 |

FOREIGN PATENT DOCUMENTS 930458  7/1963  United Kingdom .

Primary Examiner—Maurice J. Welsh
Attorney, Agent, or Firm—Peter C. Richardson; Albert E. Frost; Robert K. Blackwood

[57] ABSTRACT

Purified diisocyanate polyetherurethane prepolymers and process therefor. Polyetherurethane urea polymers prepared by mixing said prepolymers with an aqueous solution of an amino, ureido or hydroxy substituted amine or a like-substituted alpha-amino acid, and a method of using same as a space filling adhesive sealant in surgery.

68 Claims, No Drawings

POLYETHERURETHANE UREA POLYMERS AS SPACE FILLING TISSUE ADHESIVES

BACKGROUND OF THE INVENTION

The present invention is directed to purified diisocyanate polyetherurethane prepolymers, a process therefor, polyetherurethane urea polymers prepared by mixing said prepolymers with an aqueous solution of an amino, ureido, or hydroxy substituted amine or a like-substituted alpha-amino acid, and a method of using said polymers as a space filling adhesive in surgery.

Protection of the central nervous system (CNS) from aberrant peripheral influences partly stems from the physiological compartmentalization. The main function of the cranial meninges and the cerebrospinal fluid (CSF) is to provide support and protection for the brain, in addition to that afforded by the calvaria.

The brain, having approximately the same specific gravity as the CSF, floats in the fluid thus being cushioned against momentary contortions by external forces. The surgical treatment of the CNS diseases, correction of CNS malformations, the care and repair of traumatic lesions of CNS, and the surgical palliation of pain and abnormal motor movements all require a disruption of the CNS homeostasis. Elimination of the extracranial communication resulting from neurologic surgery is required to preserve or restore the maximal degree of neurologic function possible with the disease state. The watertight closure of the dural incisions (especially when the dura contracts) and dural defects is accomplished with mixed success by suturing the dura with silk, sometimes with fascia or pericranium grafts. When the normal CSF pathway is violated and there is continuity between subarachnoid space and the skin and mucous membranes, there is an inherent risk of retrograde infection of the CNS system. Unsuccessful dural closure leads to CSF leaks and menningitis, side effects that are the bane of the surgical therapy of CNS disease. Several neurosurgical and otorhinolaryngological procedures are often accompanied by severe and sometimes fatal complications resulting from CSF rhinorrhea and/or otorrhea. Thus in the surgical therapy of CNS disease as well as in the otorhinolaryngological surgery of the head and neck there is a need for a permanent, space filling adhesive sealant to close dura in a watertight fashion, and to fill sinuses and cranial bone defects. The adhesive should be applicable as a viscous liquid which can be sculpted. Once hardened in place, it should be somewhat rubbery, not brittle and subject to shattering. It should comprise relatively high molecular weight molecules which cannot diffuse away from the site of application. Final polymerization in place should occur in the range of room temperature and physiological temperature with minimal or no generation of heat, and without significant shrinkage. Finally, the adhesive should be reproducibly prepared and non-toxic.

Luting agents, for filling cavities or spaces in human or other animal bones, comprising the reaction product of a polyetherurethane diisocyanate prepolymer, a curing agent and a filler, have been disclosed by Oechsle, U.S. Pat. No. 4,477,604. Exemplary of his prepolymers, which are not purified, is one derived by reacting "tolylene diisocyanate" (presumably toluene 2,4-diisocyanate) with polytetramethyleneglycol in 1.7 to 1 molar ratio at elevated temperature, conditions conducive to side reactions (e.g., branching and cross-linking). The key to that earlier invention lies in the mixing of equal volumes of the prepolymer and a preformed mixture of a filler (50–75%) and a curing agent (25–50%). Exemplary is a mixture composed of 50% of the same polytetramethyleneglycol used in the prepolymer, 30% butane (1,4?)-diol and 20% methylene bis dipropylaniline, a toxic substance. The prepolymer is crude and the interaction is therefore complicated by the fact that the prepolymer still contains the original excess of the toluene diisocyanate. The latter substances, as well as lower molecular weight amines derived therefrom, are toxic. In any event, based on isocyanate numbers, it is evident that the large volume of reactive curing agents and less reactive filler will provide a large molar excess of the toxic curing agent. In marked contrast, the space filling adhesive polymer of the present invention contains no filler, no excess of toxic chain extenders, and no toxic, lower molecular weight diisocyanates or derived diamines. It is formed from molar equivalents of a purified diisocyanate prepolymer, which is highly homogeneous in structure, and a generally much lower volume of an aqueous solution of the chain extender (curing agent). Thus incorporation of the chain extender compound into the polymer is substantially complete. In the most preferred embodiment of the present invention, a non-toxic, natural L-aminoacid is employed as chain extender.

British Patent No. 930,458 (1961) describes extractive methods for removing mixed toluene 2,4- and 2,6-diisocyanates from highly branched and cross-linked, structurally heterogeneous urethane polyisocyanates and isocyanurates. Davis et al., U.S. Pat. No. 3,415,790 describes the removal of phenyl-1,4-diisocyanate from structurally heterogeneous prepolymers (obtained by heating co-polyether glycols with said phenyl diisocyanate at 97°), with varying degrees of success, by extraction with propylene carbonate, acetonitrile or cyclohexane. The resulting prepolymers were in turn reacted with water and/or a diamine and wet spun into thread.

Rabizzoni, U.S. Pat. No. 3,883,577 prepared a highly branched and cross-linked, structurally heterogeneous prepolymer from mixed toluene diisocyanates and trimethylolpropane in acetonitrile at less than 40° C., then heating at 60° C. until the NCO number dropped to the desired level. The unreacted toluene diisocyanate was incompletely removed from the acetonitrile solution of prepolymer by a countercurrent type extraction with heptane. Acetonitrile was in turn removed by heating at 90° C., ultimately in vacuum, to produce a product containing 0.3% toluene diisocyanates.

Alternatively, according to U.S. Pat. No. 4,385,171 unreacted toluene diisocyanates were removed from highly branched and cross-linked, structurally heterogeneous polymers derived by heating said toluene diisocyanates and polyether polyols by a codistillation method at 100° C. The assay for residual toluene diisocyanates employed a petroleum ether extraction process. In another alternative method, Marams et al., U.S. Pat. No. 4,169,175 reduced toluene diisocyanates in similar such polymers from 2–3% to 1.0±0.2 by selective absorption of the toluene diisocyanates on a zeolite (type X molecular sieve) column.

SUMMARY OF THE INVENTION

We have now discovered certain valuable polyetherurethane-urea type polymers which meet the criteria detailed above, for use as a space filling adhesive sealants in neurosurgery, otorhinolaryngological surgery and plastic reconstructive surgery. These alloplastic biomaterials are prepared by mixing two components immediately before application. These components are (a) a purified diisocyanate polyetherurethane prepolymer incorporating (i) di(4-isocyanatophenyl)methane [diphenylmethane 4,4'-diisocyanate], di(4-isocyanatocyclohexyl)methane [dicyclohexylmethane 4,4'-diisocyanate], 1,4-diisocyanatocyclohexane [cyclohexane 1,4-diisocyanate], 4-(4-isocyanatocyclohexyl)cyclohexyl isocyanate [dicyclohexane 4,4'-diisocyanate], di(4-isocyanatophenyl)ether [diphenylether 4,4'-diisocyanate], or di(4-isocyanatocyclohexyl)ether; and (ii) a polypropyleneglycol or polytetramethaleneglycol of average molecular weight in the range of about 650–5000; in which the organic diisocyanate (i) and the polyetherglycol (ii) are incorporated predominantly in a 2:1 molar ratio; and (b) an aqueous solution comprising, for each mol of diisocyanate prepolymer, substantially one mol of a bifunctional chain extending compound of the formula

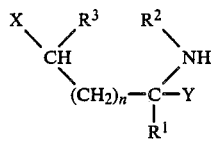
(I)

wherein
n is zero or an integer from 1–8;
X is —OH, —NHC(NH)NH$_2$ or —NHR;
Y is hydrogen or —COOH;
R is hydrogen or (C$_1$–C$_3$)alkyl;
R$^1$ is hydrogen or (C$_1$–C$_3$)alkyl; and
R$^2$ and R$^3$ are taken separately, and
R$^2$ is hydrogen or (C$_1$–C$_3$)alkyl; and
R$^3$ is hydrogen or (C$_1$–C$_3$)alkyl; or
R$^2$ and R$^3$ are taken together and are —CH$_2$—, with the proviso that when R$^2$ and R$^3$ are so taken, n is 1, 2 or 3;

or a pharmaceutically acceptable cationic or acid addition salt thereof.

The preferred adhesives are made from purified prepolymers which have been derived from di(4-isocyanatophenyl)methane or di(4-isocyanatocyclohexyl)methane and polytetramethyleneglycol of average molecular weight in the range of 650–3000. The range of 900–1100 is even more preferred. The most preferred adhesives are made from purified diisocyanate prepolymers which incorporate the diisocyanate and the polytetramethylene glycol substantially in 2:1 molar ratio, e.g., 85% 2:1, the balance being primarily 3:2.

Most preferred chain extending compounds are natural amino acids: L-lysine, L-ornithine, L-arginine, L-serine, L-homoserine or L-hydroxyproline, most particularly L-lysine. Also preferred are diamines of the formula H$_2$NCH$_2$(CH$_2$)$_n$CH$_2$NH$_2$, particularly ethylenediamine or heptamethylenediamine.

The present invention is also directed to a method of surgical repair of a skull cavity or a dural incision in a human or animal with such a space filling adhesive (said cavity caused by trauma or created in a surgical procedure); a package comprising, in physically separated compartments or containers for convenient mixing immediately prior to use as a space filling tissue adhesive, (a) said purified diisocyanate polyetherurethane prepolymer; and (b) an aqueous solution of substantially an equimolar quantity of a chain extending compound of the formula (I); a method of preparing said prepolymer; a method of purifying said prepolymer; and said purified prepolymer per se.

DETAILED DESCRIPTION OF THE INVENTION

The present invention is readily carried out. The polyetherurethane diisocyanate prepolymer, in liquid form, is derived from said polyether glycol and said organic diisocyanate, schematically represented as follows:

2OCN—Z—NCO+HO—(polyether)—OH→OCN—Z—NHCOO—(polyether)—OCONH—Z—NCO where Z is an organic hydrocarbon diradical of the formula

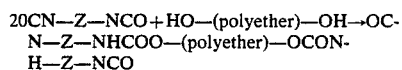

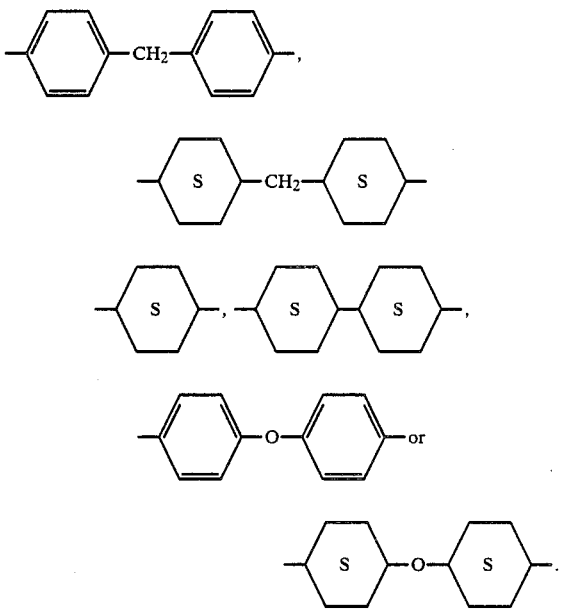

The coupling of the reagents is carried out so as to achieve substantially complete conversion of the polyether diol to a polyetherurethane diisocyanate which incorporates predominantly diisocyanate and polyether glycol, in 2:1 ratio without significant branching or cross-linking. The desired result is generally achieved by use of a moderate excess (e.g. 2–4 fold) of the organic diisocyanate. Completeness of the conversion is determined by $^{13}$C-nmr assay for residual —CH$_2$OH groups as described in specific examples below. The coupling is generally carried out in a reaction inert solvent, such as methylene chloride or toluene, optionally in the presence of a catalyst such as dibutyltin dilaurate. Since the solvent is ultimately removed by stripping in vacuum, lower boiling solvents are preferred. Toluene and methylene chloride are suitable solvents. Most preferred is methylene chloride, which is not only low boiling, but produces particularly clean products. Temperature of the coupling is quite critical, e.g., temperatures from 15°-30° C. are generally preferred. At lower temperatures, reaction times tend to be excessive. At higher temperatures, undesired branching or cross-linking or self-polymerization of the organic diisocyanate, tends to occur. However, ambient temperature is most convenient, generally producing particularly clean products in a reasonable time period (e.g., 8-16 days, depending upon the reactivity of the reactants, and, if added, the level of catalyst).

As used herein, the expression reaction-inert solvent refers to a solvent which will not interact with starting materials, intermediate or products in a manner which will adversely affect the yield or quality of the product. Relatively non-polar aprotic solvents are preferred. Polar aprotic solvents (e.g., dimethyl sulfoxide), commonly used in the preparation of polyetherurethane diisocyanate prepolymers, generally lead to undesired side reactions and impure products, and should be avoided.

All steps involved in the further isolation and purification of the prepolymer as described below are carried out at 30° C. or lower, in order to avoid side reactions (e.g. cross-linking) as discussed above.

The crude prepolymer, containing excess of the organic diisocyanate as its principal impurity, is obtained by stripping the solvent in vacuo. A key to the present invention is the discovery that the excess of the undesired organic diisocyanate can be removed by continuous extraction of an acetonitrile (optionally containing up to 25% toluene) solution of the crude prepolymer with petroleum ether, preferably one having a boiling point range within the range of 30°-60° C. Complete removal of the organic diisocyanate is determined by suitable assay of the residual acetonitrile solution of prepolymer, e.g., by reacting an aliquot of the prepolymer with an excess of a lower molecular weight alcohol (e.g. benzyl alcohol) so as to form a low molecular weight bis urethane amenable to GPC assay. Once the extraction is complete, the purified prepolymer is isolated by stripping away the acetonitrile in vacuo, ultimately for a prolonged period of time under high vacuum. Complete removal of the acetonitrile is facilitated by codistillation with a low boiling, non-toxic, reaction-inert solvent.

If desired, the purified prepolymer is rendered sterile by ultrafiltration, or more conveniently, by gamma irradiation. Finally, the prepolymer is characterized by determination of its isocyanate number (% NCO), which is used to calculate the equivalent weight of chain extender compound required in forming the space filing adhesive polymer.

The required chain extending compounds of the formula (I) above are generally known, and frequently available commercially in a form suitable for dissolution in water for direct use in the present invention. In other cases, it will be necessary to prepare the compound according to literature methods. Where stability of aqueous solutions permits, the chain extender will be predissolved in water, and packaged together with a molar equivalent of the prepolymer for mixing immediately before use as a space filling adhesive in surgical procedures. Alternatively, the calculated amount of neat chain extender compound is placed in the package, and dissolved in a specified amount of water by the user prior to mixing with the prepolymer. Subject to the degree of solubility of the chain extender in water, high concentrations are preferred.

To prepare the present polymeric adhesive, equimolar quantities of the prepolymer and the aqueous solution of chain extender are combined in a suitable vessel, preferably with the less viscous aqueous solution of chain extender introduced, e.g., by syringe, below the surface of the viscous prepolymer layer, so as to avoid any possibility of splashing on initial stirring. The mixture is stirred using a high torque, variable speed electric stirrer with a paddle or other stirring means which rapidly leads to complete and thorough mixing of the 2 components within a short period of time (e.g., 1-3 minutes. If not already mixed in the barrel of a syringe (for example, if mixed in a Semkit injection style mixer, available from the Semco Division of Products Research and Chemical Corp., 5454 San Fernando Road, Glendale, Calif. 91209, found to be particularly useful for this purpose), the mixture immediately is taken up into a syringe having a large bore needle and, while still a viscous liquid, extruded into place via the syringe needle. As the polymer becomes more viscous and begins to harden, it may be worked and sculpted in place by the surgeon. If desired, to facilitate sculpting, the surface tackiness of the resulting adhesive graft is removed by irrigating the surface with an aqueous solution of an aminoacid such as L-lysine. After sculpting, any excess aminoacid solution is generally suctioned or sponged away. The polymer hardens in place, generally within 5-10 minutes of mixing. In the case of the polymers employing an L-aminoacid as chain extender, the set time can be increased, if desired, by decreasing the pH of the aqueous solution of the L-aminoacid.

For a given weight of prepolymer, the mols of prepolymer diisocyanate are calculated by use of the following formula:

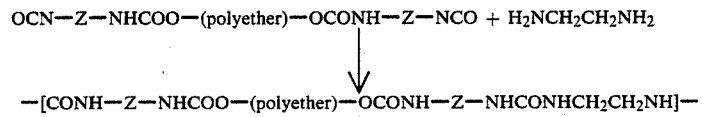

$$\text{No. Mols} = \text{Wt. (g.)} \times \frac{\% \text{ (NCO)}}{100} \times \frac{1}{2} \times \frac{1}{42 \text{ g/mol}}$$

The factor ½ reflects the fact that each molecule of prepolymer contains two NCO groups, while 42 is the molecular weight of each NCO group.

Interaction of the prepolymer and chain extender (e.g., ethylenediamine) is schematically represented as follows:

$$\text{OCN—Z—NHCOO—(polyether)—OCONH—Z—NCO} + \text{H}_2\text{NCH}_2\text{CH}_2\text{NH}_2$$
$$\downarrow$$
$$-[\text{CONH—Z—NHCOO—(polyether)—OCONH—Z—NHCONHCH}_2\text{CH}_2\text{NH}]-$$

In principle, all free NCO groups are converted to urea (or related groups depending upon the exact nature of the chain extending compound) in the formation and hardening of the space filling adhesive.

The present space filling adhesive finds extensive use in surgical procedures in mammals, including man. On mixing prior to application, the surgeon obtains a viscous, transparent, clear liquid, having good adhesive properties which allow rapid, well-sealed closure of the dura without undue tissue deformation, and having excellent space filling properties which allow rapid closure of traumatic or iatrogenic bony defects. Once in place, the polymer can be immediately and easily contoured and handled, generally hardening within several minutes to provide a smooth surface. The following is a list of surgical procedures where the present space filling adhesive fills the need for a watertight closure of dural incisions or defects, with or without fascia graft, or to fill cavities in bone, including the skull:

supratentorial gliomas and meningiomas;
tumors of cerebellopontine angle;
posterior fossa tumors (cerebellar astrocytomas; glomus jugulare tumors of the temporal bone);
trans-sphenoidal approach to sellar and parasellar tumors, and third ventricular tumors;
transcranial approach to orbital tumors;
the base of the skull tumors by transbasal approach;
meningeal fistulas;
repair of CSF rhinorrhea from cribriform plate or roof of the ethmoid;
repair of the CSF rhinorrhea from the sphenoid sinus;
osteoplastic frontal sinus obliteration and nasofrontal duct obstruction;
comminuted fractures of the anterior and/or posterior wall of frontal sinus;
orbital floor blowout fractures;
trauma of anterior cranial fossa flor;
mastoid air cell occlusion in suboccipital approach to cerebellopontine angle;
occlusion of the posteromedial air-cell tract in the posterior wall of the internal auditory meatus;
ossicular reconstruction.

The present space filling adhesive is readily tested in vivo by use in such surgical procedures in experimental animals, and readily tested in vitro using suitable inanimate models.

The present invention is illustrated by the following examples. However, it should be understood that the invention is not limited to the specific details of these examples.

A. POLYETHERURETHANE-DIISOCYANATE PREPOLYMERS

EXAMPLE A1

Purified 2:1 Di(4-isocyanatocyclohexyl)methane: Polytetramethyleneglycol-1000 Prepolymer. Run A Under argon at ambient temperature, a dry reaction flask of 13 liter capacity was equipped with a mechanical stirrer. The flask was charged with 580 g. (2.2 mol) of di(4-isocyanatocyclohexyl)methane (dicyclohexylmethane-4,4′-diisocyanate) and 500 ml. of $CH_2Cl_2$, and stirred to dissolve. The resulting solution was diluted with 5000 ml. of $CH_2Cl_2$ followed by a solution of 1070 g. (1.05 mol) of polytetramethyleneglycol-1000 (i.e., of average molecular weight 1000) in 2300 ml. $CH_2Cl_2$, and finally made up to 12 liters total volume with additional $CH_2Cl_2$. Dibutyldilauryltin catalyst (0.1 ml.) was added and the mixture stirred for 14 hours before adding a second, like portion of catalyst. The mixture was stirred for 17 days, by which time no unreacted polytetramethylene remained according to the $C^{13}$-nmr method described below. The methylene chloride was removed in vacuo by use of a continuous feed rotary evaporator, and the residual crude prepolymer taken up in 750 ml. $CH_3CN$, and reevaporated to remove any remaining $CH_2Cl_2$. The second residue was taken up in 1000 ml. fresh $CH_3CN$ and transferred to a standard liquid-liquid extraction apparatus designed for continuous extraction of a heavier liquid with a lighter liquid, and continuously extracted with petroleum ether for 20 days, by which time no remaining monomeric diisocyanate in the prepolymer, according to the assay described below. The bulk of the $CH_3CN$ was removed under vacuum by means of a continuous feed rotating evaporator, ultimately for 78 hours at 0.1 mm/Hg, the flask rotating once per minute to facilitate full removal of the solvent. The prepolymer was transferred under argon to three 500 ml. stoppered flasks, and sterilized by irradiation with 3.01–3.2 Mrads of Co-60 gamma rays. %NCO, 3.16; viscosity, 66,400 CPS; $M_w$, 10,298; $M_n$ 6,170; $M_w/M_n$, 1.669; $M_z$, 18,492; $^{13}$C-nmr (CDCl$_3$) includes major peaks at 26.0, 26.6, 27.6, 32.2, 33.5, 64.5, 70.6 and 155.8 ppm.

To determine completeness of reaction, a dry 25 ml. one-necked round bottom flask was equipped with a magnetic stirrer. The flask was charged with a 10 ml. aliquot of the polyetherurethane prepolymer reaction. The solution was concentrated on a dry rotary evaporator. The residual prepolymer was dissolved in 3–4 ml. of dry $CDCl_3$. The solution was filtered in a dry box under argon into a dried NMR tube. The $^{13}$C NMR spectrum was obtained with a minimum of 90,000 scans and a pulse delay of 0.1–0.5 sec. The spectral region between 77.0 ppm (chloroform) and 55 ppm was vertically and horizontally expanded and compared to the analogous region of the starting polytetramethyleneglycol. When the carbon signal of the terminal —$CH_2OH$ of the latter, located at 62.5 ppm, was not detected in the reaction spectrum, the reaction was considered complete.

To determine complete extraction of monomeric diisocyanate, a dry 25 ml. flask was equipped with a magnetic stirrer. The flask was charged with a 0.1–0.2 ml. aliquot of prepolymer/acetonitrile solution undergoing the continuous extraction, 2 ml. of methylene chloride, 0.25 ml. of dry benzyl alcohol, and 0.010 ml. of $Bu_2Sn(lauryl)_2$. The solution was allowed to stir under argon overnight (16h) at room temperature. The derivatized sample was diluted with HPLC grade methylene chloride and filtered. To a 0.1–0.2 ml. aliquot of the derivatized sample solution was added 1–10 mg. of di-(4-isocyanatocyclohexyl)methane bis(benzyl)urethane (HBBU, Preparation 1) to make an enhanced sample, which was diluted with HPLC grade $CH_2Cl_2$, filtered, and analyzed by GPC under the following conditions: 100 A ultrastyragel column, 1.0 ml/min. of methylene chloride, U.V. and R.I. detectors, and the Nelson Analytical X-TRA CROM software package. The extraction was considered complete when there was no evidence of the HBBU in the derivatized sample. This was performed by comparing the horizontally and vertically expanded region of the HBBU retention time in both the derivatized and the enhanced sample.

To determine the %NCO (NCO number), eight dry 150 ml. Erlenmeyer flasks were tared and equipped with a magnetic stirrer. Six flasks were charged with 0.3–1.0 g. of prepolymer and weighed on an analytical balance. Two flasks were used for the control experiment. All flasks were charged with 25–30 ml. of toluene. Each flask (samples and controls) was treated with 5 ml. of a 6% dibutylamine/toluene solution. The samples were allowed to stir under argon at room temperature for 30 minutes. Each solution was diluted with isopropanol (reagent grade, 100 ml.). The solutions were titrated with 0.05N or 0.1N HCl to the yellow endpoint using bromophenol blue as an indicator. The percentage isocyanate was calculated as follows:

$$(V_b - V_s)N(4.202)/m = \% \text{ NCO}$$

where
Vb = volume HCl to titrate blank
Vs = volume HCl to titrate sample
N = normality of the HCl
m = mass of the prepolymer The percentage isocyanate was calculated in a standard manner by averaging the results of the titration of the six samples.

To measure viscosity, a dry 10 ml. or 20 ml. syringe barrel was filled with the prepolymer. The syringe was secured using clamps and Brookfield viscometer spindles were lowered into the neat prepolymer. The measurements were then performed utilizing spindle no. 7.

Molecular weights were determined by GPC. A dry 10 ml. round bottom flask was equipped with a magnetic stirrer. The flask was charged with 0.1 g. of prepolymer, 3 ml. of methylene chloride, and 0.25 ml. of benzylamine. The reaction was allowed to stir under argon at room temperature overnight (16h). The reaction mixture was diluted with HPLC grade methylene chloride and filtered. The sample was analyzed by GPC under the following conditions: 1000 and 500A ultrastyragel columns; 1 ml/min. of methylene chloride; R.I. detector; and the X-TRA CHROM software package. The Mw/Mn determinations were performed with the XTRA-CHROM software. The molecular weight standards used were polystyrene: 36000, 15000, 3500 and 2350.

EXAMPLE A2

Purified 2:1 Di(4-isocyanatocyclohexyl)methane: Polytetramethyleneglycol-1000 Prepolymer. Run B Using the method of Example A1, a solution of 400 g. (1.53 mol) of di-(4-isocyanatocyclohexyl)methane in 1000 ml. $CH_2Cl_2$ was diluted with 732 g., (0.72 mol) of polytetramethyleneglycol-1000 in 3000 ml. $CH_2Cl_2$ and the mixture diluted to 12 liters with $CH_2Cl_2$. The reaction, which was catalyzed with 0.125 ml. of $Bu_2Sn(lauryl)_2$, was stirred for 12 days, the prepolymer isolated, purified and sterilized according to Example A1. %NCO, 2.00; viscosity 125,000 cps; Mw, 10,455; Mn, 6,650; Mw/Mn 1.572; Mz, 16,807; IR ($CHCl_3$) includes peaks at 3425, 3050, 2950, 2850, 2775, 2250 and 1725 $cm^{-1}$.

EXAMPLE A3

Purified 2:1 Di(4-isocyanatophenyl)methane: Polytetramethyleneglycol-1000 Prepolymer A dry 12 liter flask, equipped with a mechanical stirrer was charged with a solution of di-(4-isocyanatophenyl)methane (922 g., 3.78 mols) in 2500 ml. of $CH_2Cl_2$, followed by a solution of polytetramethyleneglycol-1000 (1280 g., 1.25 mols) in 2500 ml. of $CH_2Cl_2$. The reaction mixture was stirred under argon for 16 days, by which time no unreacted polytetramethylene glycol could be detected by $^{13}$C-nmr as described in Example A1. The $CH_2Cl_2$ was stripped, displaced with $CH_3CN$ as in Example A1 and finally dissolved in 2000 ml. $CH_3CN$. The $CH_3CN$ solution was continuously extracted with petroleum ether for 25 days, by which time no free di-(4-isocyanatophenyl)methane could be detected by the GPC assay of Example A1 (substituting butanol for benzyl alcohol and di-(4-isocyanatophenyl)methane bis(butyl)urethane (Preparation 2) in place of HBBU). Following continuous extraction, the $CH_3CN$ solution was concentrated as in Example A1 to produce purified title prepolymer in substantially quantitative yield; $^{13}$C-nmr includes peaks at 153.5, 135.7, 128.9, 124.3, 118.6, 70.3, 64.7, 40.4 and 26.4 ppm; $^1$H-nmr (DMSO-$d_6$) includes peaks at 9.5 (bs), 8.55 (bs), 7.12 (q), 4.05 (t), 3.8 (bs), 3.6 (t), 1.75 (m) and 1.47 (m) ppm; $M_w$ 8993, $M_n$ 7397, $M_w/M_n$ 1.216, $M_z$ 10735.

EXAMPLE A4

Purified 2:1 Di(4-isocyanatophenyl)methane: Polytetramethyleneglycol-1000 Prepolymer A mixture of di-(4-isocyanatophenyl)methane (27.5 g., 0.110 mols) and polytetramethyleneglycol (average molecular weight 1000; 55 g., 0.055 mol) in 400 ml. of toluene was stirred for 2 weeks. The toluene was stripped to produce a residue of crude prepolymer containing unreacted diisocyanate by HPLC assay. The crude product was taken up in 80 ml. of acetonitrile and 20 ml. of toluene and the resulting solution continuously extracted with petroleum ether having a boiling point range of 30–60° C. for 3.5 days. The acetonitrile layer was stripped to yield purified title prepolymer in substantially quantitative yield, having properties identical to the product of Example A3. The present example was repeated using di(4-isocyanatophenyl)methane (279.7 g., 2.24 mols) and polytetramethyleneglycol (average molecular weight 1000; 543.8 g., 1.07 mols) in 4 liters of toluene to yield, after purification by continuous extraction, purified title prepolymer having equivalent physical properties.

EXAMPLE A5

Purified 2:1 Di(4-isocyanatocylohexyl)methane: Polytetramethyleneglycol-3000 Prepolymer Title product is prepared by the method of Example A1, substituting a molar equivalent of polytetramethyleneglycol-3000 for the polytetramethyleneglycol-1000.

EXAMPLE A6

Purified 2:1 Di(4-isocyanatocyclohexyl)methane: Polypropyleneglycol-1000 Prepolymer Title product is prepared by the method of Example A1, substituting a molar equivalent of polypropyleneglycol-1000 for the polytetramethyleneglycol-1000.

EXAMPLE A7

Purified 2:1 1,4-Disocyanatocyclohexane Polytetramethyleneglycol-1000 Prepolymer Title product is prepared by the method of Example A1, substituting a molar equivalent of 1,4-diisocyanatocyclohexane for the di(4-isocyanatocyclohexyl)methane.

EXAMPLE A8

Purified 2:1 Di(4-isocyanatocyclohexyl)ether: Polytetramethyleneglycol-1000 Prepolymer Title product is prepared by the method of Example A1, substituting a molar equivalent of di(1,4-isocyanatocyclohexyl)ether for the di(4-isocyanatocyclohexyl)methane.

B. SPACE FILLING ADHESIVE, POLYETHERURETHANE UREA POLYMERS

EXAMPLE B1

Space Filling Adhesive Polymer from the Prepolymer of Example A1 and L-Lysine

For in vivo testing, the barrel of a 20 cc syringe, supported in a vertical position, was charged with 11.4 g. of the prepolymer of Example A1 (3.16% NCO, 4.28 mmols, 8.56 mequivs. of —NCO) and 0.82 ml. of aqueous L-lysine (8 g./10.5 ml. of solution, 4.28 mmols, 8.56 mequivs. of —NH$_2$), preferably injected to the bottom of the syringe barrel to preclude splashing on initial stirring. Using a vortex mixer attached to the shaft of a variable speed electric motor, the components were mixed for 2.25 minutes at 270 rpm. The mixer was removed and the polymer immediately extruded through a 13G needle to the site of a surgical procedure in a test mammal to form an adhesive graft. The surface of the graft was irrigated with additional of the aqueous L-lysine to eliminate surface tackiness, graft sculpted and contoured, and the excess aqueous L-lysine suctioned off. The adhesive was immediately hardened in place in 5–9 minutes. Material was separately formed into a disc suitable for determination of nmr; $^{13}$C-nmr (solid state) includes peaks at 26.8, 72.7, 111.0, 114.7, 114.9, 118.5, 118.7, 122.2, 163.0, 163.6, 164.1 and 164.7 ppm. $^{13}$C-nmr (pyridine-d$_5$) includes peaks at 176.3, 158.4, 157.6, 156.6, 70.8, 64.2, 50.3, 33.7, 32.6 and 27.4 ppm.

An equimolar quantity of the calcium salt of L-lysine in saturated aqueous solution was substituted for L-lysine as the chain extender, with equivalent results.

EXAMPLE B2

Space Filling Adhesive Polymer from the Prepolymer of Example A3 and L-Lysine

For in vivo testing, the barrel of 20 cc syringe, supported in a vertical position, was charged with 12.6 g. of the prepolymer of Example A3 (3.09% NCO, 4.63 mols, 9.27 mequivs. of —NCO) and 0.89 ml. of aqueous L-lysine (8 g. of L-lysine mixed with 5 ml. of H$_2$O gives 10.5 ml. of aqueous L-lysine; 4.63 mmols, 9.27 mequivs. of —NH$_2$), preferably injected to the bottom of the syringe barrel. Using a vortex mixer attached to the shaft of a variable speed electric motor, the components were mixed for 2.25 minutes at 270 rpm. The mixer was removed and the polymer immediately extruded through a 13G needle to the site of a surgical procedure in a test mammal, where it was immediately contoured and hardened in place in 3–7 minutes. Material was molded in vitro for determination of physical properties; $^{13}$C-nmr (pyridine-d$_5$) includes peaks at 154.8, 151.6, 151.5, 129.8, 119.4, 70.9, 64.9, 41.1, 27.3 ppm.

The set time of the title polymer was incrementally increased by incrementally reducing the pH of the lysine solution with concentrated HCl.

EXAMPLE B3

Space Filling Adhesive Polymer from the Prepolymer of Example A1 and Ethylenediamine Present title polymer was made according to the method of Example B1, substituting 4.28 mmols (256.8 mg.) of ethylenediamine in 257 mg. of H$_2$O for the aqueous L-lysine.

EXAMPLE B4

Space Filling Polymer from the Prepolymer of Example A1 and 1,7-Diaminoheptane

Present title polymer was made according to the method of Example B1, substituting 4.28 mmols (556 mg.) of 1,7-diaminoheptane in 0.55 g. of H$_2$O for the aqueous L-lysine.

EXAMPLE B5

Space Filling Polymer from the Prepolymer of Example A3 and Ethylenediamine

Present title polymer was made according to the method of Example B2, substituting 4.62 mmols (278 mg.) of ethylenediamine in 278 mg. of H$_2$O for the aqueous L-lysine.

EXAMPLE B6

Space Filling Adhesive Polymer from the Prepolymer of Example A3 and 1,7-Diaminoheptane Title prepolymer was made by the method of Example B2, substituting 4.63 mmols of 1,7-diaminoheptane (602 mg.) in 0.6 g. of H$_2$O for the aqueous L-lysine.

EXAMPLE B7

Space Filling Adhesive Polymer from the Prepolymer of Example A1 and L-Serine

Present title product was made according to the method of Example B1, substituting 4.28 mmols (450 mg.) of L-serine in saturated H$_2$O solution for the aqueous L-lysine.

EXAMPLE B8

Space Filling Adhesive Polymer for the Prepolymer of Example A1 and L-Ornithine

Present title product was made according to the method of Example B1, substituting 4.28 mmols (566 mg.) of L-ornithine in saturated aqueous solution for the aqueous L-lysine.

EXAMPLE B9

Space Filling Adhesive Polymer from the Prepolymer of Example A1

Present title product was prepared according to the method of Example B1, substituting 4.28 mmols (746 mg.) of L-arginine in saturated aqueous solution for the aqueous L-lysine.

EXAMPLE B10

Space Filling Adhesive Polymer from the Prepolymer of Examples A5, A6, A7 and A8 and L-lysine Present title products are prepared according to the method of Example B1, substituting a molar equivalent of appropriate prepolymer (based on its isocyanate number) for the prepolymer of Example A1.

PREPARATION 1

Di-(4-isocyanatocyclohexyl)methane:bis-(Benzyl)urethane (HBBU)

A dry, 50 ml. one-necked round bottom flask was equipped with a magnetic stirrer. The flask was charged with 30 ml. of dry methylene chloride, 2 g. (0.0076 mol) of HMDI, 2.1 g. (2 ml., 0.019 mol) benzyl alcohol, and 0.010 ml. of Bu$_2$Sn(lauryl)$_2$. The reaction was allowed to stir overnight (16h) under argon at room temperature. The volatiles were removed on a rotary evaporator. The resulting white powder was washed with ethyl ether and dried under vacuum. This product was employed in determining the completeness of diisocyanate monomer extraction (see Example A1 above).

PREPARATION 2

Di-(4-isocyanatophenyl)methane:bis-(Butyl)urethane

By the method of the preceding Preparation, di-(4-isocyanatophenyl)methane (1.13 g., 5 mmols) and 1-butanol (1.34 g., 18 mmols) were reacted to form present title product, isolated as a white powder in like manner, but without ether wash. This product was used in determining the completeness of diisocyanate monomer extraction (see Example A3 above).

I claim:

1. A space filling tissue adhesive which comprises a polyetherurethane urea polymer formed by reaction of a purified diisocyanate polyetherurethane prepolymer with an aqueous solution comprising, for each mol of diisocyanate prepolymer, substantially one mol of a chain extending compound of the formula

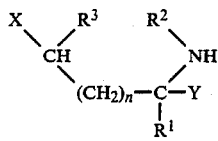

wherein
n is zero or an integer from 1–8;
X is —OH, —NHC(NH)NH$_2$ or —NHR;
Y is hydrogen or —COOH;
R is hydrogen or (C$_1$–C$_3$)alkyl;
R$^1$ is hydrogen or (C$_1$–C$_3$)alkyl; and
R$^2$ and R$^3$ are taken separately, and
R$^2$ is hydrogen or (C$_1$–C$_3$)alkyl; and
R$^3$ is hydrogen or (C$_1$–C$_3$)alkyl; or
R$^2$ and R$^3$ are taken together and are —CH$_2$—, with the proviso that when R$^2$ and R$^3$ are so taken, n is 1, 2 or 3;

or a pharmaceutically acceptable cationic or acid addition salt thereof; said purified prepolymer having been previously formed by reacting di(4-isocyanatophenyl)methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl)ether with a polypropyleneglycol or polytetramethyleneglycol of average molecular weight in the range of about 650–5000; and comprised predominantly of individual molecules consisting of said reactants in 2:1 molar ratio, respectively.

2. An adhesive of claim 1 wherein the prepolymer is formed by reacting di(4-isocyanatophenyl)methane or di(4-isocyanatocyclohexyl)methane with polytetramethyleneglycol of average molecular weight in the range of 650–3000.

3. An adhesive of claim 2 wherein the polytetramethyleneglycol is of average molecular weight in the range of 900–1100 and the prepolymer is comprised substantially of individual molecules consisting of the diisocyanato and polytetramethyleneglycol reactants in 2:1 molar ratio, respectively.

4. An adhesive of claim 3 wherein the diisocyanato compound is di(4-isocyanatophenyl)methane.

5. An adhesive of claim 3 wherein the diisocyanato compound is di(4-isocyanatocyclohexyl)-methane.

6. An adhesive of claim 3, wherein the chain extending compound is L-lysine, L-ornithine, L-arginine, L-serine, L-homoserine, or L-hydroxyproline.

7. An adhesive the claim 6 wherein the chain extending compound is L-lysine.

8. The adhesive of claim 4 wherein the chain extending compound is L-lysine.

9. The adhesive of claim 5 wherein the chain extending compound is L-lysine.

10. An adhesive of claim 3 wherein the chain extending compound is

H$_2$NCH$_2$(CH$_2$)$_n$CH$_2$NH$_2$

11. An adhesive of claim 10 wherein the chain extending compound is ethylenediamine or heptamethylenediamine.

12. The adhesive of claim 4 wherein the chain extending compound is ethylenediamine.

13. The adhesive of claim 5 wherein the chain extending compound is ethylenediamine.

14. The adhesive of claim 4 wherein the chain extending compound is heptamethylenediamine.

15. The adhesive of claim 5 wherein the chain extending compound is heptamethylenediamine.

16. A method surgical repair of a skull cavity or a dural incision, in a human or animal, which comprises the steps of: (a) producing a viscous polymerizing liquid by reacting a purified diisocyanate polyetherurethane prepolymer with an aqueous solution comprising, for each mol of diisocyanate prepolymer, substantially one mol of a chain extending compound of the formula

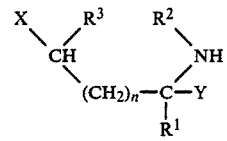

wherein
n is zero or an integer from 1–8;
X is —OH, —NHC(NH)NH$_2$ or —NHR;
Y is hydrogen or —COOH;
R is hydrogen or (C$_1$–C$_3$)alkyl;
R$^1$ is hydrogen or (C$_1$–C$_3$)alkyl; and
R$^2$ and R$^3$ are taken separately; and
R$^2$ is hydrogen or (C$_1$–C$_3$)alkyl; and
R$^3$ is hydrogen or (C$_1$–C$_3$)alkyl; or
R$^2$ and R$^3$ are taken together and are —CH$_2$—, with the proviso that when R$^2$ and R$^3$ are so taken, n is 1, 2 or 3; or a pharmaceutically acceptable cationic or acid addition salt thereof; said purified prepolymer having been previously formed by reacting di(4-isocyanatophenyl)methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl)ether with a polypropyleneglycol or polytetramethyleneglycol of average molecular weight in the range of about 650–5000; and comprised predominantly of individual molecules consisting of said reactants in 2:1 molar ratio, respectively;

(b) while still in liquid form, filling said cavity or covering said dural incision with said viscous liquid to form an adhesive graft; and (c) allowing said adhesive graft to solidify and adhere to adjoining tissue in place.

17. A method of claim 16 wherein the prepolymer is formed by reacting di(4-isocyanatophenyl)methane or di(4-isocyanatocyclohexyl)methane with polytetramethyleneglycol of average molecular weight in the range of 650-3000.

18. A method of claim 17 wherein the polytetramethyleneglycol is of average molecular weight in the range of 900-1100 and the prepolymer is comprised substantially of individual molecules consisting of the diisocyanate and polytetramethyleneglycol reactants in 2:1 molar ratio, respectively.

19. A method of claim 18 wherein the diisocyanato compound is di(4-isocyanatophenyl)methane.

20. A method of claim 18 wherein the diisocyanato compound is di(4-isocyanatocyclohexyl)methane.

21. A method of claim 18, wherein the chain extending compound is L-lysine, L-ornithine, L-arginine, L-serine, L-homoserine or L-hydroxyproline.

22. A method of claim 21 wherein the chain extending compound is L-lysine.

23. The method of claim 19 wherein the chain extending compound is L-lysine.

24. The method of claim 20 wherein the chain extending compound is L-lysine.

25. A method of claim 16 which, following step (b), further comprises the steps of irrigating the surface of the adhesive graft with an aqueous solution of the same or a different chain extending compound; and sculpting and/or contouring the adhesive graft while still in viscous liquid form.

26. A method of claim 21 which, following step (b), further comprises the steps of irrigating the surface of the adhesive graft with an aqueous solution of L-lysine, L-ornithine, L-arginine, L-serine, L-homoserine or L-hydroxyproline; and sculpting and/or contouring the adhesive graft while still in viscous liquid form.

27. The method of claim 24 which, following step (b), further comprises irrigating the surface of the adhesive graft with an aqueous solution of L-lysine; and sculpting and/or contouring the adhesive graft while still in viscous liquid form.

28. A method of claim 18 wherein the chain extending compound is

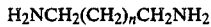

H$_2$NCH$_2$(CH$_2$)$_n$CH$_2$NH$_2$

29. A method of claim 28 wherein the chain extending compound is ethylenediamine or heptamethylenediamine.

30. The method of claim 19 wherein the chain extending compound is ethylenediamine.

31. The method of claim 20 wherein the chain extending compound is ethylenediamine.

32. The method of claim 19 wherein the chain extending compound is heptamethylenediamine.

33. The method of claim 20 wherein the chain extending compound is heptamethylenediamine.

34. A package comprising, in physically separated compartments or containers for convenient reaction by mixing immediately prior to use as space filling tissue adhesive, (a) a purified diisocyanate polyetherurethane prepolymer previously formed by reacting di(4-isocyanatophenyl) methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl) ether with a polypropyleneglycol or polytetramethyleneglycol of average molecular weight in the range of about 650-5000; and comprised predominantly of individual molecules consisting of said reactants in 2:1 molar ratio, respectively; and (b) an aqueous solution, or a solid for dissolution in water prior to use, comprising, for each mol of diisocyanate prepolymer, substantially one mol of a chain extending compound of the formula

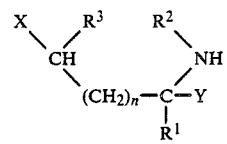

wherein n is zero or an integer from 1-8;

X is —OH, —NHC(NH)NH$_2$ or —NHR;

y is hydrogen or —COOH;

R is hydrogen of (C$_1$–C$_3$)alkyl;

R$^1$ is hydrogen or (C$_1$–C$_3$)alkyl; and

R$^2$ and R$^3$ are taken separately; and

R$^2$ is hydrogen or (C$_1$–C$_3$)alkyl; and

R$^3$ is hydrogen or (C$_1$–C$_3$)alkyl; or

R$^2$ and R$^3$ are taken together and are —CH$_2$—, with the proviso that when R$^2$ and R$^3$ are so taken, n is 1, 2 or 3;

or a pharmaceutically acceptable cationic or acid addition salt thereof.

35. A package of claim 34 wherein the prepolymer is formed by reacting di(4-isocyanatophenyl)methane or di(4-isocyanatocyclohexyl) methane with polytetramethyleneglycol of average molecular weight in the range of 650-3000.

36. A package of claim 35 wherein the polytetramethyleneglycol is of average molecular weight in the range of 900-1100 and the prepolymer is comprised substantially individual molecules consisting of the diisocyanato and polytetramethyleneglycol reactants in 2:1 molar ratio, respectively.

37. A package of claim 36 wherein the diisocyanato compound is di(4-isocyanatophenyl)methane.

38. A package of claim 36 wherein the diisocyanato compound is di(4-isocyanatocyclohexyl)methane.

39. A package of claim 36, wherein the chain extending compound is L-lysine, L-ornithine, L-arginise, L-serine, L-homoserine or L-hydroxyproline.

40. A package the claim 39 wherein the chain extending compound is L-lysine.

41. The package of claim 37 wherein the chain extending compound is L-lysine.

42. The package of claim 38 wherein the chain extending compound is L-lysine.

43. A package of claim 36 wherein the chain extending compound is

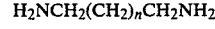

H$_2$NCH$_2$(CH$_2$)$_n$CH$_2$NH$_2$

44. A package of claim 43 wherein the chain extending compound is ethylenediamine or heptamethylenediamine.

45. The package of claim 37 wherein the chain extending compound is ethylenediamine.

46. The package of claim 38 wherein the chain extending compound is ethylenediamine.

47. The package of claim 37 wherein the chain extending compound is heptamethylenediamine.

48. The package of claim 38 wherein the chain extending compound is heptamethylenediamine.

49. A method of purifying a crude diisocyanate polyurethane prepolymer formed by reacting di(4-isocyanatophenyl)methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl)ether with a polypropyleneglycol or polytetramethyleneglycol of average molecular weight in the range of about 650-5000; comprised of unreacted diisocyanato compound and prepolymer, the latter comprised predominantly of individual molecules consisting of said reactants in 2:1 molar ratio, respectively, which comprises the steps of:

(a) dissolving the crude prepolymer in acetonitrile containing up to 25% toluene by volume;

(b) removing said unreacted diisocyanato compound by continuously extracting the resulting solution with petroleum ether having a boiling point range in the range of 30°-60° C.; and (c) recovering said prepolymer in purified form.

50. A method of claim 49 wherein the crude prepolymer is formed by reacting di(4-isocyanatophenyl)methane or di(4-isocyanatocyclohexyl)methane with polytetramethyleneglycol of average molecular weight in the range of 650-3000.

51. A method of claim 50 wherein the polytetramethyleneglycol is of average molecular weight in the range of 900-1100 and the prepolymer is comprised substantially individual molecules consisting of the diisocyanato and polytetramethyleneglycol reactants in 2:1 molar ratio.

52. The method of claim 51 wherein the diisocyanate is di(4-isocyanatophenyl)methane.

53. The method of claim 51 wherein the diisocyanate is di(4-isocyanatocyclohexyl)methane.

54. A purified diisocyanate polyetherurethane prepolymer formed by reacting di(4-isocyanatophenyl)methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl)ether with a polypropyleneglycol or polytetramethyleneglycol of average molecular weight in the range of about 650-5000; comprised predominantly of individual molecules consisting of the diisocyanato and polyetherglycol reactants in 2:1 molar ratio, and which is substantially free of the diisocyanato reactant.

55. A prepolymer of claim 54 formed by reacting di(4-isocyanatophenyl)methane or di(4-isocyanatocyclohexyl)methane and polytetramethyleneglycol of average molecular weight in the range of 650-3000.

56. A prepolymer of claim 55 wherein the polytetramethyleneglycol is of average molecular weight in the range of 900-1100 which is comprised substantially of individual molecules consisting of the diisocyanato and polytetramethyleneglycol reactants in 2:1 molar ratio, respectively.

57. The prepolymer of claim 56 wherein the diisocyanate is di(4-isocyanatophenyl)methane.

58. The prepolymer of claim 56 wherein the diisocyanate di(4-isocyanatocyclohexyl)methane.

59. A method of preparing a diisocyanate polyurethane prepolymer which comprises reacting a 2-4 molar excess of di(4-isocyanatophenyl)methane, di(4-isocyanatocyclohexyl)methane, 1,4-diisocyanatocyclohexane, 4-(4-isocyanatocyclohexyl)cyclohexyl isocyanate, di(4-isocyanatophenyl)ether or di(4-isocyanatocyclohexyl)ether with a polypropyleneglycol or polytetramethyleneglycol of average molecular weight in the range of about 650-5000, at 15°-30° C. in a non-polar aprotic solvent until reaction is substantially complete, said prepolymer comprised predominantly of individual molecules consisting of the diisocyanate and polyetherglycol reactants in 2:1 molar ratio, respectively.

60. A method of claim 59 wherein the prepolymer is prepared by reacting di(4-isocyanatophenyl)methane or di(4-isocyanatocyclohexyl)methane with polytetramethyleneglycol of average molecular weight in the range of 650-3000.

61. A method of claim 60 wherein the polytetramethyleneglycol is of average molecular weight in the range of 900-1100 and the prepolymer is comprised substantially of individual molecules consisting of the diisocyanato and polytetramethyleneglycol reactants in 2:1 molar ratio, respectively.

62. The method of claim 61 wherein the diisocyanate is di(4-isocyanatophenyl)methane.

63. The method of claim 61 wherein the diisocyanate is di(4-isocyanatocyclohexyl)methane.

64. A method of claim 59 wherein the solvent is toluene or $CH_2Cl_2$.

65. A method of claim 60 wherein the solvent is $CH_2Cl_2$.

66. A method of claim 61 wherein the solvent is $CH_2Cl_2$.

67. The method of claim 62 wherein the solvent is $CH_2Cl_2$.

68. The method of claim 63 wherein the solvent is $CH_2Cl_2$.

* * * * *